US005611347A

United States Patent [19]
Davidson

[11] Patent Number: 5,611,347
[45] Date of Patent: Mar. 18, 1997

[54] ZIRCONIUM OXIDE AND ZIRCONIUM NITRIDE COATED PERCUTANEOUS DEVICES

[75] Inventor: James A. Davidson, Germantown, Tenn.

[73] Assignee: Smith & Nephew, Inc., Memphis, Tenn.

[21] Appl. No.: 467,629

[22] Filed: Jun. 6, 1995

Related U.S. Application Data

[60] Division of Ser. No. 112,587, Aug. 26, 1993, Pat. No. 5,496,359, which is a continuation-in-part of Ser. No. 919,932, Jul. 27, 1992, Pat. No. 5,282,850, which is a continuation-in-part of Ser. No. 830,720, Feb. 4, 1992, Pat. No. 5,258,022, which is a continuation-in-part of Ser. No. 557,173, Jul. 28, 1990, Pat. No. 5,152,794, which is a continuation-in-part of Ser. No. 385,285, Jul. 25, 1989, Pat. No. 5,037,438.

[51] Int. Cl.$^6$ ..................................................... A01B 5/04
[52] U.S. Cl. ............................................................. 128/697
[58] Field of Search ..................................... 128/897–899

[56] References Cited

U.S. PATENT DOCUMENTS

| | | |
|---|---|---|
| 2,987,352 | 6/1961 | Watson et al. . |
| 3,643,658 | 2/1972 | Steinemenan . |
| 3,677,795 | 7/1972 | Bokros et al. . |
| 3,685,059 | 8/1972 | Bokros et al. ................. 623/2 |
| 3,969,130 | 7/1976 | Bokros ........................... 623/2 |
| 4,040,129 | 8/1977 | Steinemenan et al. . |
| 4,145,764 | 3/1979 | Suzuki et al. . |
| 4,159,358 | 6/1979 | Hench et al. . |
| 4,223,412 | 9/1980 | Aoyagi et al. . |
| 4,495,664 | 1/1985 | Blanquaert . |
| 4,608,051 | 8/1986 | Reck et al. . |
| 4,617,024 | 10/1986 | Broemer et al. . |
| 4,652,459 | 3/1987 | Engelhardt . |
| 4,652,534 | 3/1987 | Kasuga . |
| 4,671,824 | 6/1987 | Haygarth ........................ 148/6.11 |
| 4,687,487 | 8/1987 | Hintermann . |
| 4,714,474 | 12/1987 | Brooks, Jr. et al. . |
| 4,728,488 | 3/1988 | Gillett et al. . |
| 4,778,461 | 10/1988 | Pietsch et al. ................. 623/2 |
| 4,822,355 | 4/1989 | Bhuvaneshwar . |
| 4,834,756 | 5/1989 | Kenna . |
| 4,955,911 | 9/1990 | Frey et al. . |
| 5,037,438 | 8/1991 | Davidson . |
| 5,061,278 | 10/1991 | Bicer . |

FOREIGN PATENT DOCUMENTS

| | | |
|---|---|---|
| 770080 | 10/1967 | Canada . |
| 1140215 | 1/1983 | Canada . |
| 38902 | 11/1981 | European Pat. Off. . |
| 0159410 | 12/1984 | European Pat. Off. . |

(List continued on next page.)

OTHER PUBLICATIONS

O'Connor, Leo, "Novacor's VAD: How to Mend a Broken Heart," Mechanical Engineering, Nov. 1991 pp. 53–55.
Korane, Kenneth, "Replacing the Human Heart," Machine Design, Nov. 7, 1991, pp. 100–105.

(List continued on next page.)

*Primary Examiner*—William E. Kamm
*Attorney, Agent, or Firm*—Pravel, Hewitt, Kimball & Krieger

[57] ABSTRACT

Percutaneous implants fabricated from a core or substrate of a low modulus metal coated with blue to black zirconium oxide or zirconium nitride. The coating provides enhanced thrombogenicity, biocompatibility, blood compatibility, corrosion-resistance, friction and microfretting resistance, durability, and electrical insulation, where applicable. The coatings may be applied to low modulus metallic substrates by physical or chemical vapor deposition as well as other ion-beam assisted methods. Preferably, however, for optimizing attachment strength, the percutaneous implants are fabricated from zirconium or zirconium-containing alloys and the coatings are formed by oxidizing or nitriding through an in situ method that develops a coating from and on the metal surface of the percutaneous implant, without need for depositing a coating on the metal surface.

12 Claims, 3 Drawing Sheets

FOREIGN PATENT DOCUMENTS

| | | |
|---|---|---|
| 0410711A1 | 7/1990 | European Pat. Off. . |
| 1943801 | 4/1970 | Germany . |
| 2134926 | of 0000 | Germany . |
| 2811603 | 3/1978 | Germany . |
| 8939 | 4/1986 | Japan . |
| 180679 | 7/1986 | Japan . |
| 1325269 | 8/1973 | United Kingdom . |
| 2206182 | 5/1987 | United Kingdom . |

OTHER PUBLICATIONS

Baruah Bileaflet Mechanical Cardioc Valve Prosthesis, "Instructions for Use" brochure (Author and date unknown).

Pamphlet, "Zircadyne Corrosion Properties," Teledyne Wah Change Albany (no date) pp. 1–16.

Conte, Borello, and Cabrini, "Anodic Oxidation of Zircaloy–2," Journal of Applied Electrochemistry, vol. 6, pp. 293–299 (1976).

Budinski, K.G., "Tribological Properties of Titanium Alloys," vol. 1, *Wear of Materials*, AMSE (1991) pp. 289–299.

Bill, R.C., "Selected Fretting–Wear–Resistant Coatings for Ti–6%Al–%Allo Wear" 106 (1985), pp. 283–301.

Bertrand, G., et al., "Morphology of Oxyde Scales Formed on Titanium," vol. 21, *Oxidation of Metals*, Nos. 1/2 (1983),, pp. 1–19.

More, R.B., Silver, M.D., "Pyrolytic Carbon Prosthetic Heart Valve Occluder Wear: In Vivo vs. In Vitro Results for the Bjork–Shiley Prosthesis," *Journal of Applied Biomaterials*, vol. 1, pp. 267–278 (1990).

Kowbel, W., et al., "Effect of Boron Ion Implantation on Tribological Properties of CVD $Si_3N_4$," vol. 46, *Lubrication Engineering*, 10 pp. 645–650.

Author Unknown, "Boric Acid: A self–replenishing solid lubricant," Tex Spotlight, Advanced Materials and Processes, pp. 40–42 (Jul. 1991).

"Increase in Biocompatibility of Polymers by Treatment with Phosphatidyl Choline," Study done by Bicompatibles, Ltd., U.K. and Wolfson Centre for Materials Technology Brunel University (Jul. 1991).

Golomb, G., et al., "Prevention of bioprosthetic heart valve tissue calcification by charge modification: Effects of protamine binding by formaldihyde," vol. 25, *J. of Biomedical Materials Research*, pp. 85–98 (1991).

Akins, Cary W., "Mechanical Cardiac Valvular Prostheses," Current Review by the Society of Thoracic Surgeons, pp. 161–172 (1991).

Haygarth and Fenwick, "Improved Wear Resistance of Zirconium by Enhanced Oxide Films," Thin Solid Films, Metallurgical, and Protective Coatings, vol. 118, pp. 351–362 (1984).

"The Cementless Fixation of Hip Endoprosthesis," edited by Morscher, Mittelmeier, Total Hip Replacement with the Autophor Cement–Free Ceramic Prosthesis, pp. 225–241 (1984).

Brown and Merritt, "Evaluation of Corrosion Resistance of Biology," Dept. of Biomedical Engineering, Case Western Reserve University, Feb. 13, 1986 (1:8).

Davidson, et al., "Wear, Creep and Frictional Heating of Femoral Implant Articulating Surfaces and the Effect on Long–Term Performance—Part II, Friction, Heating, and Torque," J. of Biomedical Materials Research: Applied Biomaterials,, vol. 22, No. A1, pp.

ASTM F86–84, "Standard Practice for Surface Preparation and Marking of Metallic Surgical Implants," pp. 12–14 (1984), corrected editorially in May 1987.

Kruschov, "Principles of Abrasive Wear," Wear 28, 69–88 (1974).

Weightman and Light, "The Effect of the Surface Finish of Alumina and Stainless Steel on the Wear Rate of UHMW Polyethylene," Biomaterials, 7, 20–24 (1986).

Viegas, et al., "Metal Materials Biodegration: A Chronoamperometric Study," *J. of Materials Science: Materials in Medicine 1*, 105–109 (1990).

Briscoe, et al., "The Friction and Wear of High Density Polythene: The Action of Lead Oxide and Copper Oxide Fillers," *Wear* 27, 19–34 (1974).

Rabinowicz, "Lubrication of Metal Surface by Oxide Films," ASLE Translations, 10, 400–407 (1967).

Mausli, et al., "Constitution of Oxides on Titanium Alloys for Surgical Implants," *Advances in Bio Materials*, 8, p. 305 (1988).

Rokicki, "The Passive Oxide Film on Electropolished Titanium" (Feb. 1990).

Coll and Jacouot, "Surface Modification of Medical Implants and Surgical Devices Using TiN Layers," *Surface and Coatings Technology*, 36, p. 867 (1988).

Bradhurst and Heuer, "The Influence of Oxide Stress on the Breakaway Oxidation of Zircaloy–2," *J. of Nuclear Materials*, 37, p. 35 (1970).

Demizu, et al., "Dry Friction of Oxide Ceramics Against Metals: The Effect of Humidity," *Tribology Transactions*, 33, p. 505 (1990).

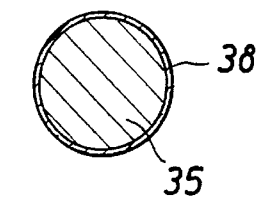
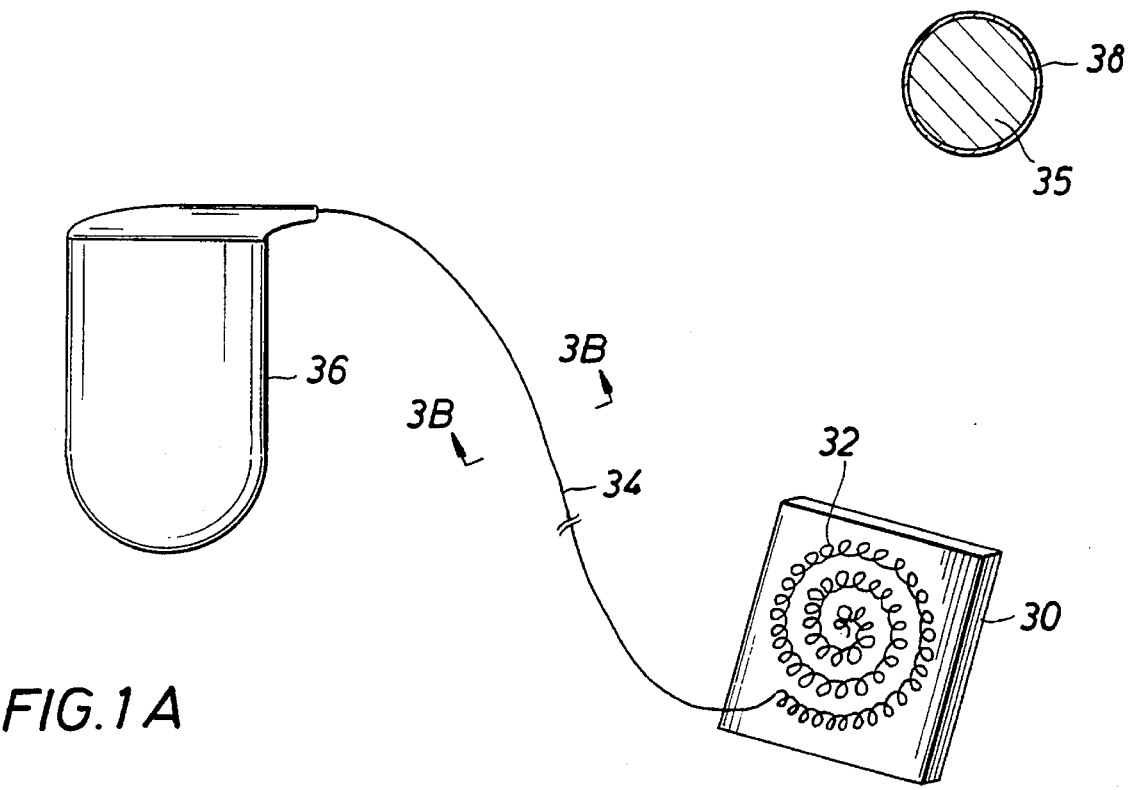
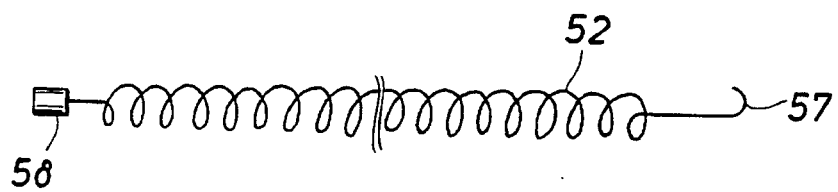

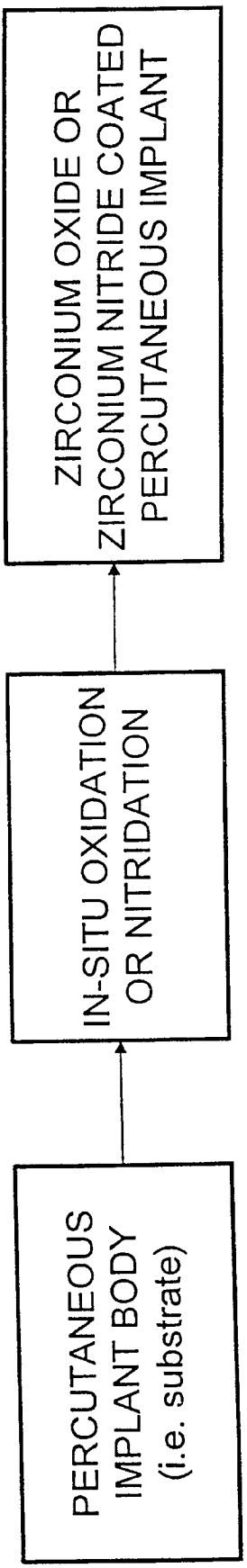
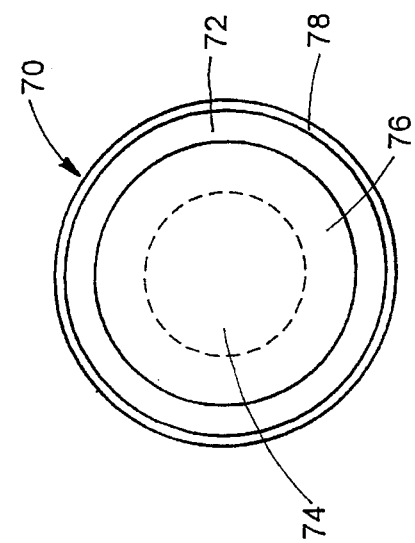
FIGURE 4C
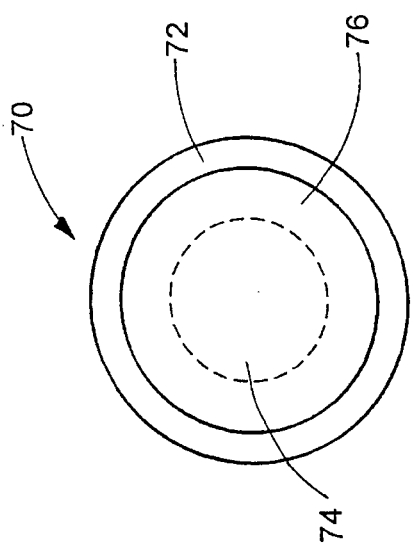
FIGURE 4B
FIGURE 4A

5,611,347

ZIRCONIUM OXIDE AND ZIRCONIUM NITRIDE COATED PERCUTANEOUS DEVICES

RELATED APPLICATIONS

This is a division of application Ser. No. 08/112,587, filed Aug. 26, 1993, issued as U.S. Pat. No. 5,496,359, which is a continuation-in-part of U.S. Ser. No. 07/919,932, filed Jul. 27, 1992, issued as U.S. Pat. No. 5,282,850, which is in turn a continuation-in-part of U.S. Ser. No. 07/830,720, filed Feb. 4, 1992, issued as U.S. Pat. No. 5,258,022, which is a continuation-in-part of Ser. No. 07/557,173, filed Jul. 23, 1990, issued as U.S. Pat. No. 5,152,794, which is in turn a continuation-in-part of U.S. Ser. No. 07/385,285, filed Jul. 25, 1989, issued as U.S. Pat. No. 5,037,438.

BACKGROUND OF THE INVENTION

1. Field of the Invention

The invention is of percutaneous implants of enhanced biocompatibility, blood compatibility, and corrosion resistance. More specifically, the invention implants are fabricated from relatively low modulus metals, such as zirconium or a zirconium-containing alloy, and are coated with blue to black zirconium oxide or zirconium nitride to provide enhanced blood compatibility, microfretting resistance, electrical insulation, and corrosion resistance where applicable.

2. Description of the Related Art

With advances in the technology for treating heart diseases, there has developed an increasing demand for sophisticated cardiovascular implants and surgical tools for use in cardiovascular surgery.

Certain cardiac treatment procedures require the use of pacemaker leads and other current-bearing leads that are usually coated with an insulative barrier that both electrically insulates and isolates the current-bearing core from body fluids. Currently, a typical pacemaker or other cardiovascular lead includes a central core of electrically conductive metal, usually cobalt-nickel alloy, coated with a polymeric insulative coating, usually polyurethane. However, polyurethane coatings eventually break down under the effect of body fluids and enzymes producing potentially harmful degradation products. Further, the polymer coating may crack or separate with time so that body fluids or adjacent wires come in contact with the electrical conductor and interfere with electrical signals. Further, the electrical conductor is then subject to corrosion due to body fluids.

In a typical defibrillator, a flexible silicone polymeric patch with a thinly coiled titanium, cobalt-nickel, or stainless steel wire is attached to the appropriate segment of heart muscle. A lead wire is attached to this coil for powering the coil to stimulate the heart muscle. The lead wire exits from the body to an external power source. The lead wire is frequently coated with polyurethane. Thus, this lead wire is both an electrical carrying device and a percutaneous device, in the sense that it penetrates the skin and exits from the body. However, it is coated with a relatively soft and fragile polymeric composition which provides limited protection to potential damage to lead sections carried outside the body. Thus, there is a need for a percutaneous lead that is crush resistant, biocompatible, and that provides suitable electrical conductance and insulation to isolate the electrical carrying lead from other lead wires and body tissue. Further, the lead should be resistant to chemical degradation in body fluids.

SUMMARY OF THE INVENTION

The invention provides improved percutaneous implants fabricated from a low modulus metallic material, such as zirconium and zirconium-containing alloys, covered with a biocompatible, microfretting and corrosion-resistant, hemocompatible, electrically insulative coating of blue to black zirconium oxide or yellow to orange zirconium nitride. These coatings are tightly adherent to the underlying metal and are of a sufficient thickness to provide the desired electrical insulation, blood compatibility, microfretting resistance, and corrosion resistance, as may be required for the particular percutaneous implant.

In one embodiment, the invention provides electrical signal carrying leads for use in a living body. These leads carry a signal from a source, sometimes external to the body, to or from an organ, such as the heart, to provide a therapeutic effect. Alternatively, for diagnostic applications, a signal may be carried by a sensor from an organ of the body to an external device for recording the signal or for otherwise using the signal. Thus, the invention provides, for instance, sensor, pacemaker, and defibrillator leads that are ductile and of high strength while providing biocompatibility, blood compatibility, and resistance to corrosion in body fluids. These pacemaker, sensor, and defibrillator leads include a central core of a low modulus electrically conductive metallic composition, such as zirconium or zirconium-containing alloys, covered with an electrically insulative, abrasion-resistant coating that is tightly adherent to the core. These coatings are resistant to corrosion by body fluids so that their useful life exceeds that of polyurethane coated leads which are subject to corrosion and degradation by body fluids with subsequent interference with electrical signals. The invention also provides numerous other electrical signal bearing leads coated with blue to black zirconium oxide or zirconium nitride.

In another embodiment, the invention provides percutaneous devices fabricated from low modulus alloy metallic compositions, such as zirconium and zirconium-containing alloys, that have enhanced biocompatibility, hemocompatibility, durability, stability, and crush resistance as compared to conventionally used biocompatible polymeric compositions. The invention percutaneous devices may also have surfaces covered with a coating of blue to black zirconium oxide or yellow to orange zirconium nitride to provide enhanced biocompatibility, hemocompatibility, durability, and abrasion resistance.

Furthermore, the oxide- or nitride-coated surfaces according to the invention may be coated with other compositions to further enhance biocompatibility and performance. For example, phosphatadyl choline, heparin, proteins, or other surface treatment may be applied for reducing platelet adhesion or other adverse cellular or tissue response to surfaces in contact with blood, or boronated or silver-doped hardened surface layers to reduce friction and wear if the implant is subject to microfretting or other mechanical wear. In certain instances, it may be desirable to coat the surfaces according to the invention with a medicament such as an antibiotic, anticoagulant, and the like, as needed for the particular application.

The thickness of the hard zirconium oxide or nitride coating is preferably less than about 5 microns (i.e., in the range about 3 to about 6 microns) for optimal residual compressive stresses and minimal dimensional changes or distortion during oxidation or nitridation. However, the thickness of the coating is frequently not critical where the surface coating provides enhanced hemocompatibility and biocompatibility and is not subject to forces requiring optimal residual compressive stresses. Thus, in these cases, the thickness of the coating is limited only by its own integrity, i.e., that it is not subject to cracking and spalling, thereby potentially releasing particulates into the body of the patient. Such coatings may range from about 0.1 to about 20 microns or more in thickness.

BRIEF DESCRIPTION OF THE DRAWINGS

FIG. 1A is a schematic diagram of the components of a defibrillator, showing power source, lead wire, and polymeric patch with coiled electrode.

FIG. 1B is a cross-section (coating exaggerated in dimension to show detail) of the lead wire of FIG. 3A.

FIG. 2 is a schematic of an embodiment of the invention coated pacemaker leads.

FIG. 4A is a flow sheet type diagram of a preferred in situ process for forming the zirconium oxide or zirconium nitride coating of the inventive percutaneous implants.

FIG. 4B is a cross-section schematic (not to scale) of an arbitrary-shaped percutaneous implant illustrating the implant body with layer of diffused oxygen and zirconium oxide coating.

FIG. 4C is a cross-section schematic (not to scale) of an arbitrary-shaped percutaneous device illustrating the implant body with a layer of diffused oxygen, a zirconium oxide coating, and an additional coating on the zirconium oxide coating.

DETAILED DESCRIPTION OF THE PREFERRED EMBODIMENTS

Figure 3A:
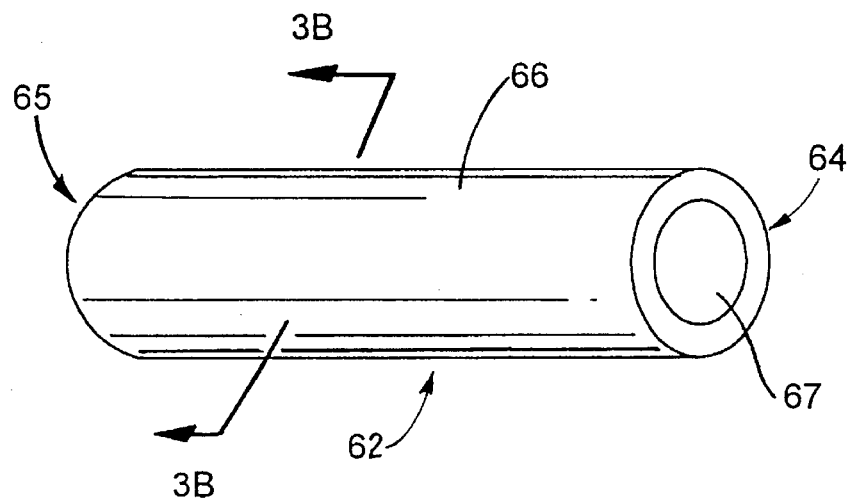
FIG. 3A is a schematic diagram of a percutaneous conduit for carrying fluids.
Figure 3B:
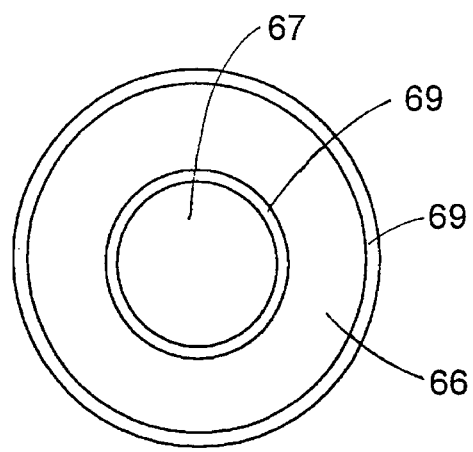
FIG. 3B is a cross-section schematic (not to scale) of the percutaneous conduit for carrying fluids of FIG. 3A along plane 3B—3B.

The invention provides low modulus metallic percutaneous implants coated with a layer of blue to black zirconium oxide or zirconium nitride. These coatings provide a blood compatible, microfretting resistant, electrically insulative, stable, and corrosion resistant ceramic coating. Furthermore, these ceramic blue to black zirconium oxide or zirconium nitride coatings may be further overlaid with a thin coating of phosphatadyl choline, heparin, or other surface treatment for further reducing platelet adhesion, if the implant will be in contact with blood. Other medicaments may also be coated onto the ceramic surfaces of the invention. The ceramic coatings of the invention may also be modified by boronation or silver doping to further improve friction and wear characteristics, if necessary.

The term "low modulus" as used to describe the metallic compositions preferred in this invention include those metallic compositions that preferably have a modulus of elasticity less than about 130 GPa.

The term "blue to black" as used to describe zirconium oxide means that the color of the oxide may range from blue to black, depending on zirconium concentration in the oxidized alloy or process conditions that produce the coating. Thus, for pure zirconium, the blue to black oxide formed by the preferred in situ process is substantially monoclinic zirconium oxide. However, if a zirconium alloy is used, then, for the useful zirconium alloys, the in situ process will produce a surface containing a mixture of oxides, but still substantially zirconium oxide, to produce the blue to black appearance. If an ion beam deposition assisted or other non-in situ process is used, such as chemical or vapor deposition, then the color of the oxide is not affected by the substrate metal. In this case, the white tetragonal or cubic $ZrO_2$ is possible as well. Such coatings are useful as "overlay" coatings on an in situ blue-black zirconium oxide or yellow-orange zirconium nitride coating. Since the hardness match between such overlays and the in situ coatings are closer than between overlay and substrate metal, the coatings are more firmly attached and have superior integrity. Other hard coatings are also useful as overlays—such as amorphous diamond-like carbon coatings, wear-resistant coatings formed by silver deposition, and lubricious boronated coatings.

The term "yellow to orange" as applied to zirconium nitride refers to the range of colors of zirconium nitride and the comments above about alloys and consequent mixtures of oxides with zirconium oxide also apply in the nitride context.

FIG. 1A shows a defibrillator including a flexible silicone polymeric patch 30 with a coil of conductive wire 32 (typically titanium, stainless steel, or cobalt-nickel-chromium) on the side of the silicone patch 30 that will contact muscle tissue. When in place in the body, the lead wire 34 that carries power to the coil 32 extends out of the body (through the skin) and is electrically connected to a power source in a protective container 36. According to the invention, the lead wire 34 is fabricated with an electrically conductive core 35 of low modulus metal, preferably zirconium or zirconium-containing alloys, and has a coating 38 of blue to black zirconium oxide or zirconium nitride. This coating, shown in exaggerated scale in FIG. 1B, electrically insulates the lead wire from electrical contact with surrounding body tissue while also protecting the metallic core from corrosion and attack by body fluids. Thus, because the invention ceramic coatings are stable, inert, and more resistant to, attack and degradation, than the currently used polymeric coatings, the lead wire has potentially longer life and is also more biocompatible, in that it does not spall or degrade with time, like polyurethane or other polymer coatings, that may interfere in a potentially harmful way with desired electrical signals.

FIG. 1B is a cross-section of the lead wire 34 showing the core of low modulus metal 35 and the thin coating of ceramic zirconium oxide or nitride 38 (thickness exaggerated to show detail). The thickness of the coating may range from 0.1 to about 20 microns or more, more preferably from about 1 to about 10 microns, most preferably about 3–6 microns.

The invention provides, as shown schematically in FIG. 2, a pacemaker wherein the conductor 52, comprising either a single wire or multiple wires, is fabricated from a low modulus metallic alloy that is coated with blue to black zirconium oxide or yellow to orange zirconium nitride, with the exception of the electrode for contacting heart muscle 57, and an optional electrode 58 at the other end of the lead for engaging the pulse generator: exposed low modulus metallic ends of the wire or wires are preferable.

I claim:

1. A percutaneous implant that penetrates the skin of a living body and thereby protrudes from the body, the implant comprising:

(a) a low elastic modulus, metallic implant body for penetrating skin tissue of a patient, said implant body having a first end for insertion into said patient, a second end for remaining outside of said patient, and a section therebetween for extending into the patient, said first end, second end and section therebetween having surfaces; and (b) a corrosion-resistant, biocompatible, hemocompatible, durable, stable coating at least partially covering the surfaces of the implant body first end and section therebetween, said coating selected from the group consisting of zirconium oxides, ranging in color from blue to black, and zirconium nitrides, ranging in color from yellow to orange.

2. The percutaneous implant of claim 1, wherein the coating is from about 1.0 to about 20 microns thick.

3. The percutaneous implant of claim 1, wherein the implant body comprises a metal selected from the group consisting of zirconium and zirconium-containing alloys.

4. The percutaneous implant of claim 3, wherein the implant body further includes a sub-surface zone containing diffused oxygen and the coating includes diffusion-bonded blue to black zirconium oxides.

5. The percutaneous implant of claim 4, wherein the coating is from about 0.1 to about 20 microns thick.

6. The percutaneous implant of claim 1, further comprising a silver-containing overlay coating over the corrosion-resistant, biocompatible, hemocompatible, durable, stable coating.

7. The percutaneous implant of claim 1, further comprising a second coating over the corrosion-resistant, biocompatible, hemocompatible, durable, stable coating, said second coating including a material selected from the group consisting of amorphous diamond-like carbon material, cubic zirconia material, and white tetragonal zirconia material.

8. The percutaneous implant of claim 1, further including a boron-containing overlay coating over the corrosion-resistant, biocompatible, hemocompatible, durable, stable coating.

9. The percutaneous implant of claim 1 further including an additional coating at least partially covering the surfaces of the implant body first end and section therebetween, said additional coating selected from the group consisting of phosphatadyl choline, heparin and proteins.

10. The percutaneous implant of claim 1 further including a medicament coating on the corrosion-resistant, biocompatible, hemocompatible, durable, stable coating.

11. The percutaneous implant of claim 10, wherein said medicament coating is an antibiotic.

12. The percutaneous implant of claim 10, wherein said medicament coating is an anticoagulant.

* * * * *